(12) United States Patent
Furton et al.

(10) Patent No.: US 11,884,233 B1
(45) Date of Patent: Jan. 30, 2024

(54) BIOMETRIC VULNERABILITY-BASED CONTROL OF A PASSENGER RESTRAINT SYSTEM ABOARD A MOTOR VEHICLE

(71) Applicant: GM GLOBAL TECHNOLOGY OPERATIONS LLC, Detroit, MI (US)

(72) Inventors: Lisa M. Furton, Beverly Hills, MI (US); Scott D. Thomas, Novi, MI (US); Dorel M. Sala, Troy, MI (US); George D. Allen, Rochester Hills, MI (US); Sean T. Coughlin, Shelby Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 17/965,390

(22) Filed: Oct. 13, 2022

(51) Int. Cl.
*B60R 22/48* (2006.01)
*B60R 21/015* (2006.01)
*A61B 5/00* (2006.01)

(52) U.S. Cl.
CPC ............ *B60R 22/48* (2013.01); *A61B 5/6893* (2013.01); *B60R 21/01544* (2014.10); *B60R 21/01552* (2014.10); *B60R 2022/4808* (2013.01)

(58) Field of Classification Search
CPC .............. B60R 22/48; B60R 21/01544; B60R 21/01552; B60R 2022/4808; A61B 5/6893
See application file for complete search history.

(56) References Cited

U.S. PATENT DOCUMENTS 11,801,774 B2 * 10/2023 Lu-Dac ................ A61B 5/6893
2023/0347800 A1 * 11/2023 Friedman ................ B60R 22/48

* cited by examiner

*Primary Examiner* — Xiao En Mo
(74) *Attorney, Agent, or Firm* — Quinn IP Law (57) ABSTRACT

A method for controlling a passenger restraint system aboard a motor vehicle includes receiving, via a controller, biometric vulnerability classifier signal(s) indicative of vulnerability characteristics of a passenger seated in an interior of the motor vehicle. In response to the biometric vulnerability classifier signal(s) and a detected vehicle event requiring an actuation of the passenger restraint system, the method includes automatically adjusting an actual capacity setting of the passenger restraint system via the controller. A motor vehicle includes a vehicle body defining a vehicle interior, a passenger restraint system positioned in the vehicle interior; and a controller operable for controlling the actual capacity setting of the passenger restraint system in accordance with the method. The passenger restraint system may include a seatbelt, a seat, and one or more airbag systems.

20 Claims, 3 Drawing Sheets

BIOMETRIC VULNERABILITY-BASED CONTROL OF A PASSENGER RESTRAINT SYSTEM ABOARD A MOTOR VEHICLE

INTRODUCTION

Within a passenger compartment or interior of a motor vehicle, a driver seat and one or more passenger seats are secured to a floor pan and surrounded by or attached to a variety of passenger restraint systems. For example, drivers and other vehicle occupants are protected from sudden decelerations or external force/impact events by a seatbelt mechanism. As appreciated in the art, a typical "three-point" lap-and-shoulder seatbelt secures a passenger to a surface of a vehicle seat while also distributing energy across the passenger's chest, shoulders, and pelvis. In addition to such seatbelts, a modern vehicle interior may also include actuatable passenger restraint systems in the form of seatbelt pretensioners, motorized seatbelts, seatbelt and energy-absorbing devices, inflatable airbag systems, adjustable head restraints, moving or inflated knee bolsters, mechanical or actuatable seat energy absorbing devices, and other possible devices.

SUMMARY

The control solutions described in detail hereinbelow relate to hardware, computer-based systems, and related control methods for adapting operation of one or more passenger restraint systems aboard a motor vehicle. In particular, the present teachings are directed to performing a biometrics-based "vulnerability" assessment and passenger classification process to individually ascertain each passenger's respective susceptibility or vulnerability to forces that would otherwise be imparted to the passenger by the restraint systems during a typical actuation or deployment thereof. As used herein, the term "actuation" refers to the activation of a system that can have either reversible or non-reversible restraint elements, while "deployment" refers to the activation of a system that generally has non-reversible restraint elements.

Orthopedic, neuromuscular, or musculoskeletal frailty, for instance, is an exemplary type of force vulnerability contemplated herein. A passenger's age, illness, injury, physical stature, physical girth, relationship between girth and stature, and various other internal or external characteristic markers may correspond to increased frailty. A frail person who is an occupant with these characteristic measurable traits in turn tends to be more vulnerable than an able-bodied individual to applied forces, regardless of source. As noted above, applied forces in the context of the present disclosure specifically encompass the types of forces imparted by the almost instantaneous, high-energy actuation of the various passenger restraint systems found in a modern vehicle interior. To that end, aspects of the solutions provided herein help identify and classify prospective or actual passengers into a suitable vulnerability class. Actual capacity settings of one or more of the vehicle systems including but not limited to passenger restraint systems are then adjusted in accordance with the passenger's vulnerability class during a subsequent restraint-triggering event.

In a representative embodiment, a method for controlling a passenger restraint system aboard a motor vehicle includes receiving, via a controller, one or more biometric vulnerability classifier signals indicative of one or more vulnerability characteristics of a passenger seated within an interior of the motor vehicle. In response to the biometric vulnerability classifier signal(s) and a detected restraint-triggering event, the controller automatically adjusts at least one actual capacity setting of the passenger restraint system(s). In this manner, the controller is better able to account for biometric vulnerabilities of each respective one of the passengers on a unique basis.

The method in one or more embodiments may include detecting the vulnerability characteristic(s) using an onboard sensor suite, with the constituent sensors of the onboard sensor suite possibly including at least one in-seat sensor connected to a vehicle seat within the interior of the motor vehicle. The onboard sensor suite may also or alternatively include at least one remote sensor and/or at least one biometric sensor, with such sensors possibly detecting the vulnerability characteristics by detecting physical appearance or motion-based characteristics of the passenger, such as breathing rate or response action to some form of impulse, or an implanted medical device.

Detecting the physical appearance of the passenger may optionally include detecting a cast, a splint, and/or a brace located on a body part of the passenger, or possibly detecting a Child Restraint Seat (CRS).

The passenger restraint system in one or more embodiments includes a seatbelt. In such a case, the method may include detecting a buckled state of the seatbelt, and automatically adjusting the actual capacity setting based at least partially on the buckled state. Adjusting the capacity setting may also include adjusting a setting a capacity of a seatbelt pretensioner and/or a seatbelt energy-absorbing device connected to the seatbelt.

In some configurations, the seatbelt contains a shoulder belt webbing portion whose position can be sensed by a remote sensor. The method in such an embodiment may include detecting the shoulder belt webbing location, and automatically adjusting the actual capacity setting based at least partially on the shoulder belt location relative to the passenger, e.g., an energy adsorption load limiter or pretensioner capacity, pretensioner actuation timing, etc.

The passenger restraint system may optionally include a deployable airbag system, in which case adjusting the capacity setting includes adjusting one or more of an inflator output, an inflated cushion depth, a deployment time, and/or a vent size of the deployable airbag system.

The passenger restraint system may include an actuatable seat system, in which case adjusting the capacity setting includes modifying the actuation characteristics of one or more of a seating surface position and a head restraint location of the adjustable seat system.

The controller in a possible implementation is operable for enforcing an airbag suppression zone (ASZ) in a defined proximity to the deployable airbag system. Adjusting the actual capacity setting in such a case may include adjusting one or more of the inflator output, the inflated cushion depth, a deployment time, and/or the vent size based on whether at least a portion of the passenger is present within the ASZ.

The method in one or more embodiments thereof includes classifying a plurality of passengers of the motor vehicle into a corresponding biometric vulnerability class, as well as adjusting the actual restraint capacity setting via the controller based on the corresponding biometric vulnerability class for the particular passenger for whom the restraint is intended to function.

A motor vehicle is also disclosed herein having a vehicle body defining a vehicle interior, a passenger restraint system positioned in the vehicle interior, and a controller. The controller is operable for controlling an actual capacity setting of the passenger restraint system. Execution of instructions by a processor of the controller causes the processor to receive the one or more biometric vulnerability classifier signals indicative of vulnerability characteristics of a passenger seated within the vehicle interior. In response to the biometric vulnerability classifier signal(s) and a detected vehicle event requiring an actuation of the passenger restraint system, the controller is configured to automatically adjust an actual capacity setting of the passenger restraint system.

The method for controlling a passenger restraint system aboard a motor vehicle according to another disclosed embodiment includes detecting vulnerability characteristics of one or more passengers of the motor vehicle using a sensor suite, with the sensor suite including at least one of (i.e., one or more of) an in-seat sensor connected to a passenger seat of the motor vehicle, a remote sensor, and a biometric sensor positioned within an interior of the motor vehicle. Detecting the vulnerability characteristics in this embodiment includes detecting one or more of a physical characteristic of the passenger, an internal characteristic of the passenger, or both using the sensor suite.

The method also includes generating one or more biometric vulnerability classifier signals indicative of vulnerability characteristics of the passenger, and also receiving the biometric vulnerability classifier signal(s) via a controller of the motor vehicle. In response to the biometric vulnerability classifier signal(s) and a detected vehicle event requiring an actuation of the passenger restraint system, the method includes automatically adjusting an actual capacity setting of the passenger restraint system via the controller, wherein the passenger restraint system includes a seatbelt, a seat, and a deployable airbag system.

Adjusting the capacity setting of the passenger restraint system in one or more embodiments includes at least one of reducing a component output of the passenger restraint system, reducing a size of an activated restraint of the passenger restraint system, reducing an applied force level of an activated restraint of the passenger restraint system, and suppressing activation of a restraint of the passenger restraint system.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

The accompanying drawings, which are incorporated into and constitute a part of this specification, illustrate implementations of the disclosure and together with the description, serve to explain the principles of the disclosure.

The appended drawings are not necessarily to scale, and may present a simplified representation of various preferred features of the present disclosure as disclosed herein, including, for example, specific dimensions, orientations, locations, and shapes. Details associated with such features will be determined in part by the particular intended application and use environment.

DETAILED DESCRIPTION

The components of the disclosed embodiments, as described and illustrated herein, may be arranged in a variety of different configurations. Thus, the following detailed description is not intended to limit the scope of the disclosure as claimed, but is merely representative of possible embodiments thereof. In addition, while numerous specific details are set forth in the following description in order to provide a thorough understanding of the embodiments disclosed herein, some embodiments can be practiced without some of these details. Moreover, for the purpose of clarity, certain technical material that is understood in the related art has not been described in detail in order to avoid unnecessarily obscuring the disclosure. Furthermore, the disclosure, as illustrated and described herein, may be practiced in the absence of an element or with an element that is not specifically disclosed herein.

Figure 1:
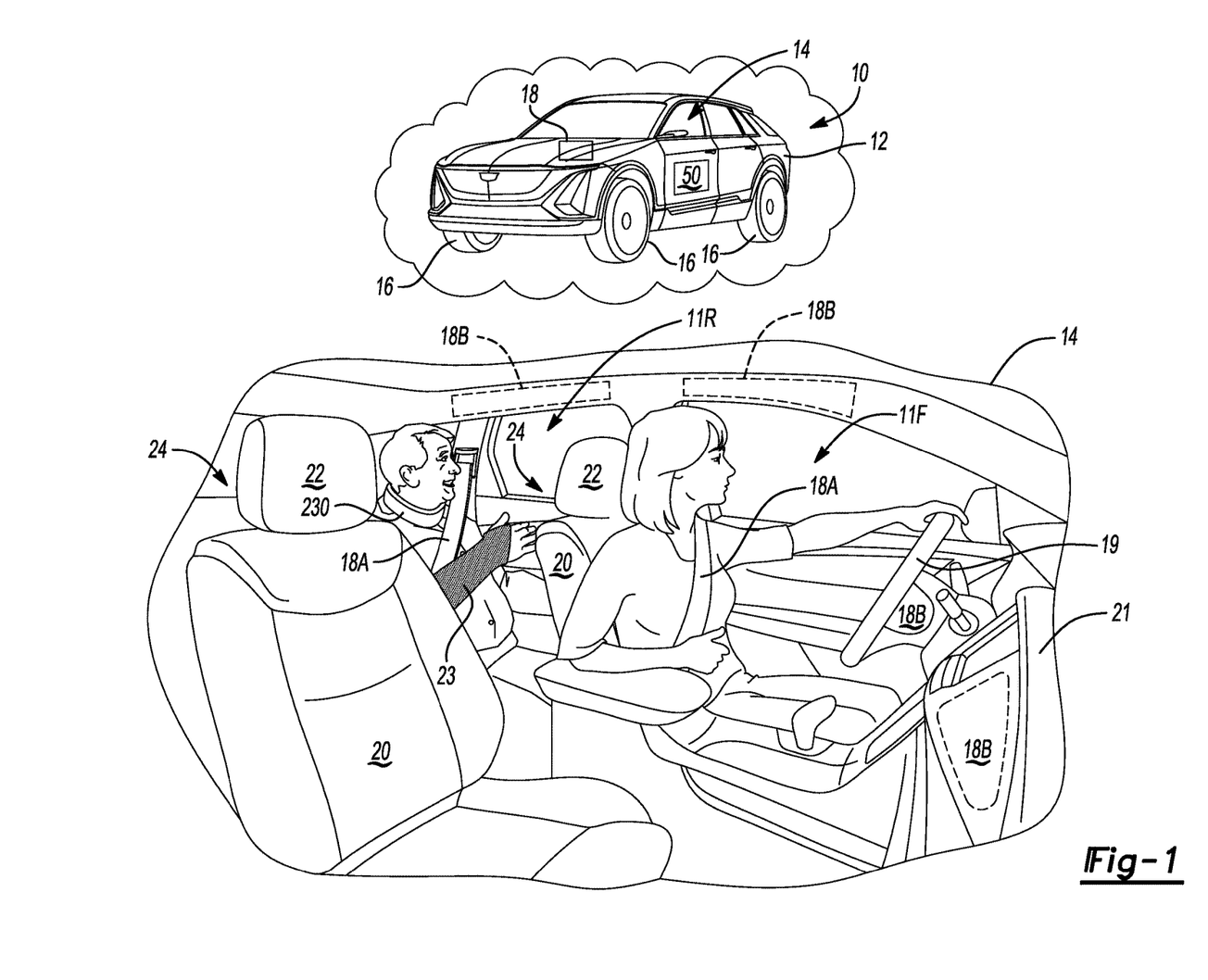
FIG. 1 schematically illustrates a motor vehicle having an interior with passenger restraint systems whose individual capacity settings are adjusted and controlled in accordance with the present disclosure.

Referring to the drawings, wherein like reference numbers refer to like features throughout the several views, FIG. 1 depicts a representative mobile system in the form of a motor vehicle 10. The motor vehicle 10 includes a vehicle body 12 defining a vehicle interior 14 and a set of road wheels 16 connected thereto. The motor vehicle 10 additionally includes one or more passenger restraint systems 18 and a controller 50 in communication therewith. Within the scope of the present disclosure, the controller 50 is configured to execute computer-readable/executable instructions in the course of performing a method 100, a non-limiting example embodiment of which is described below with reference to FIG. 3. In performing the various steps or logic blocks of the method 100, the controller 50 may ultimately adjust an actual capacity setting of one or more of the passenger restraint systems 18, with the controller 50 doing so based on an identified or classified passenger-specific vulnerability to forces imparted by actuation of the passenger restraint system 18.

The vehicle interior 14 depicted in FIG. 1 includes front and rear vehicle seats 20 on which a respective front and rear passenger 11F and 11R may be seated as shown. One or more of the passengers 11F, 11R, such as the rear passenger 11R in the non-limiting exemplary configuration of FIG. 1, has one or more physical limitations that could leave the passenger 11R more vulnerable to forces from an actuation of the passenger restraint systems 18. For instance, the rear passenger 11R could have an injured neck as indicated by a neck brace 230, an injured limb as indicated by a cast 23, or the rear passenger 11R could have other vulnerabilities brought on by illness, injury, age, size such as height to girth ratio, and the like as set forth in detail below. Each vehicle seat 20 and an adjustable head restraint 22 in turn, in one or more embodiments, may be part of an actuatable seat system 24, which in turn can be considered part of the passenger restraint system(s) 18 of the present disclosure in one or more embodiments. A capacity setting of the actuatable seat system 24 in such an embodiment may be in the form of an adjustable seating surface position of seat 20 and a head restraint location of the adjustable head restraint 22. That is, the seat(s) 20 and the corresponding head restraints 22 possibly have an adjustable capacity setting enabling the seats 20 and the head restraints 22 to function as one of the passenger restraint systems 18 within the scope of the disclosure. In a typical configuration of the motor vehicle 10, the passenger restraint systems 18 include a three-point seatbelt 18A and one or more inflatable airbag systems 18B. As appreciated in the art, such seatbelts 18A may be equipped with adjustable devices such as, e.g., a motorized pretensioner 180 and an energy-absorbing device 280 as shown schematically in FIG. 2, for the seatbelts 18A, and an inflator device 380 and one or more airbag vents 480 (FIG. 2) or one or more releasable or extendible airbag tethers 580 (FIG. 2) also possibly used with the inflatable airbag systems 18B.

Figure 2:
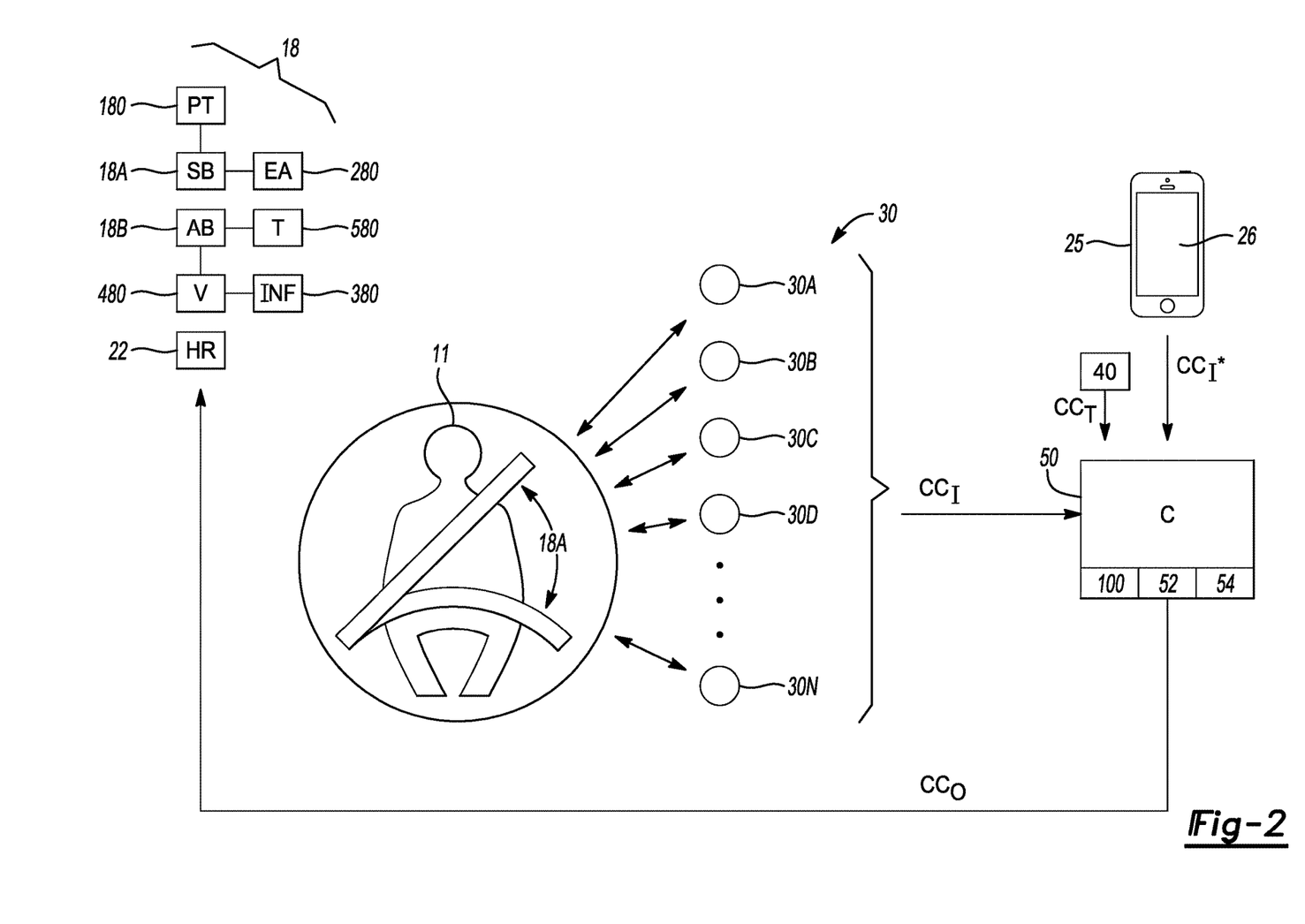
FIG. 2 is a schematic circuit diagram illustrating an exemplary control system for use aboard the motor vehicle shown in FIG. 1 when controlling passenger restraint systems(s) based on vulnerability characteristics.

As appreciated in the art, pyrotechnically-deployable, inflatable airbags such as the various airbag systems 18B shown in FIG. 2 come in a variety of forms, with a given vehicle interior 14 being equipped with one or more of the airbag systems 18B depending on the particular configuration of the motor vehicle 10. For example, the inflatable airbag systems 18B may be situated at or near a dashboard 21, typically packaged within a steering wheel 19 and one or more panels adjacent thereto or along/below/on top of a dashboard 21, along the sides of the vehicle interior 14, in a vehicle seat 20, in a vehicle door, and possibly within the fabric of the seatbelts 18A. Airbags within a seat 20 can have multiple configurations intended to restrain the occupant in the seat 20 or the passenger 11 in an adjacent seating position. Thus, the vehicle interior 14 could be equipped with frontal airbags, curtain airbags, knee airbags, seat mounted airbags, door mounted airbags, seatbelt airbags, and/or other airbags within the scope of the disclosure. Such inflatable airbag systems 18B are rapidly inflated, e.g., within about 50 milliseconds or less, with inflation typically occurring in response to a chemical charge to allow the inflating airbag system 18B to quickly fill a designated volume of the vehicle interior 14.

Referring now to FIG. 2, the controller (C) 50 is operable for receiving a biometric vulnerability classifier signal(s) (arrow $CC_1$) indicative of vulnerability characteristics of a passenger 11 seated within the vehicle interior 14 of FIG. 1. The controller 50 may be onboard the vehicle or external to the vehicle and communicate to the vehicle. The controller 50 may generate the biometric vulnerability classifier signal(s) (arrow $CC_1$) in real-time when the passenger 11 is seated within the vehicle interior 14. Alternatively, a biometric vulnerability classifier signal (arrow $CC_1^*$) may be generated offline, with both options described below. When executing the method 100, the controller 50 may communicate with each of the passenger restraint systems 18, i.e., by adapting corresponding activation levels or capacity settings thereof within a range or continuum of possible values. As shown, actual capacity of each respective one of the passenger safety systems 18 may be regulated by controlling an activation state or capacity of the seatbelt 18A, e.g., via a motorized pre-tensioner ("PT") 180 and/or an energy-absorbing ("EA") device 280, e.g., payout-based force limiting seatbelts or an inflatable seatbelt airbag as noted above. Motorized pre-tensioners or motorized payout-based force limiting level seatbelts in particular may be advantageous within the scope of the disclosure due to their adjustability, e.g., in contrast to one-time use pyrotechnic devices or other solutions.

The inflatable airbag systems 18B may include the inflator module ("INF") 380 and/or the vents ("V") 480 and releasable/extendible tethers ("T") 580. In multi-stage airbags in particular, two or more such inflator modules 380 are connected to a single inflatable airbag system 18A, with each inflator module 380 having a corresponding inflation capacity. The inflator modules 380 in some embodiments may be staged to deploy at different times, within an adjustable interval of each other, or one of the inflator modules 380 may activate and not the other. The airbag vents 480 for their part may open to a greater degree to provide a softer airbag 18B, or to a lesser degree to provide a stiffer airbag 18B. The releasable/extendable tethers 580 may restrict the airbag to a smaller inflated shape or enable a larger inflated shape.

The seats 20 may contain motorized or pyrotechnic mechanisms that can be used to move the seat 20 to a more favorable orientation during an impact event. The head restraint 22 may also move toward the occupant using a motor or pyrotechnic mechanism during such an event. In addition, any of the restraint devices can have a restraint-triggering event where the restraint devices can be initiated before an impact event, in anticipation thereof, or during the event. Some of the resettable devices could be initiated during braking, other significant vehicle maneuvers or when situations are externally detected that may result in an impact event or a significant vehicle maneuver. In addition, some of the resettable devices could be activated or have restraint capacity levels set based on detected occupant position.

In an off-line scenario, the controller 50 could obtain passenger vulnerability information from a user device 25, from historical data stored in the motor vehicle 10 or elsewhere, from vehicle personalization entries, from the cloud, from external databases with prior vulnerability data, etc. In a possible implementation, the controller 50 could receive the biometric vulnerability classifier signal(s) (arrow $CC_1^*$) from the user device 25, e.g., a tablet computer, laptop, smart phone, etc., directly or via the cloud, or from a stored database of a population of people which contains frailty indicators as appreciated in the art. For instance, a user could access a software application ("app") 26 and be prompted with a set of relevant queries regarding the physical height, weight, age, injury status, illness status, and other characteristic traits or markers, with the controller 50 receiving the biometric vulnerability classifier signal(s) (arrow $CC_1^*$) from the user device 25 or from a remote server (not shown).

In real-time/in-vehicle scenario, the controller 50 may receive the biometric vulnerability classifier signal(s) (arrow $CC_1$) from an onboard sensor suite 30, with embodiments thereof described below. In response to the biometric vulnerability classifier signal(s) (arrows $CC_1$ or $CC_1^*$) and the triggering signal(s) (arrow $CC_T$), the latter being generated by impact anticipating, force, or energy sensors 40, e.g., of an onboard sensing diagnostic module as appreciated in the art, in response to a vehicle event requiring an actuation of the passenger restraint system(s) 18, the controller 50 automatically adjusts an actual capacity setting of one or more of the passenger restraint system(s) 18 to a corresponding classification-suitable maximum permissible actuation or deployment level. That is, the controller 50 adjusts the capacity setting across a continuum rather than in a binary ON/OFF manner, based on vulnerability/frailty and optionally impact severity in lieu of using pure passenger weight-based thresholds.

In a possible offline approach, a user may provide an initial self-assessment via the app 26, which in turn is recorded as preset values in memory 54 of the controller 50. One or more passengers 11 are considered or assessed, e.g., members of the same household, relatives, friends, or any other persons whose presence in the motor vehicle 10 is expected at some point. Each time an assessed passenger 11 enters the vehicle interior 14, the controller 50 could examine the passenger 11 for vulnerability attributes, compare the same to initial baseline levels, and thereafter adjust one or more of the capacity settings of the passenger restraint systems 18 as needed to account for the vulnerabilities. Specific attributes could be collected and used to populate a reference data set, in other words, with the reference data set updated over time based on actual observed traits indicative of increased vulnerability.

As an illustrative example, the rear passenger 11R shown in FIG. 1 may have a baseline level of frailty or another vulnerability, with the controller 50 automatically applying actual capacity limits to the passenger restraint systems 18 in the passenger's proximity based on this baseline. In the event the same passenger 11R experiences an orthopedic injury, as represented in FIG. 1 by the cast 23, the controller 50 could automatically detect the cast 23 and possibly adjust the actual capacity settings for the seatbelt 18A worn by the passenger 11R and/or an airbag system 18B located in proximity to the passenger 11R.

As appreciated in the art, the sensors 40 of a typical sensing and restraint actuation or deployment system are configured to monitor or measure a host of variables, including but not necessarily limited to external impacts, wheel speeds, lateral and longitudinal accelerations, seat occupant status, seatbelt buckle status, brake pressure, steering angle, pitch, yaw, roll, entry-egress door internal pressure, etc. The sensors 40 relay electronic signals to the controller 50 as the triggering signal (arrow $CC_T$). The controller 50 analyzes the triggering signal (arrow $CC_T$) and thereafter orchestrates onboard functions of the passenger restraint systems 18, e.g., pre-tensioning of the seatbelts 18A, inflating one or more of the inflatable airbags 18B, controlling latching/unlatching states of door locks (not shown), controlling restraint capacity, etc. Thus, the controller 50 is made aware of the readings from the sensors 40 during the ongoing performance of the controller 50 while the motor vehicle 10 is in operation.

With respect to the onboard sensor suite 30 shown in FIG. 2, representative sensor devices may include, without limitation, an in-seat sensor 30A such as a pressure-detecting bladder, a resistance-detecting surface that changes state when the surface is compressed, a load cell system, and/or a capacitive sensor. As used herein, "in-seat" refers to integration with one of the vehicle seats 20 of FIG. 1, for instance embedded within the seats 20 and/or connected thereto.

The onboard sensor suite 30 may also include one or more remote sensors 30B, i.e., "remote" with respect to the passenger 11 and the vehicle seats 20. Such remote sensors 30B may be situated within the vehicle interior 14 of FIG. 1, such as by being attached to a rearview mirror (not shown), mounted to the roof (not shown), or mounted to the dashboard 21 of FIG. 1. In various possible embodiments, the remote sensors 30B could include radar, lidar, and/or ultrasound sensors, a camera, e.g., red-green-blue (RGB), RGB infrared (IR), IR, time of flight (TOF), structured light, thermal, stereo vision, etc.

Other possible sensors of the sensor suite 30 shown in FIG. 2 include biometric sensors 30C, which could be mounted to the vehicle interior 14 and/or worn by the passenger 11. Exemplary biometric data that could be measured and reported by the biometric sensors ("biosensors") 30C include a heartbeat or respiration rate of the passenger 11 or micromotions thereof, a voice, body temperature, brain waves, fingerprints, alcohol level, consumed drug level, the presence of a worn medical device, the presence of implanted medical devices such as pacemakers, other metal content inside of or outside of the body, heat, muscle activation, etc., with most of these detected values being internal characteristics of the passenger 11 or 11R.

The collective set of information from the onboard sensor suite 30 could include position data from one or more position sensors 30D, e.g., another camera or proximity detector operable for determining a position of the passenger 11 within the vehicle interior 14 of FIG. 1 As noted below, such data could be combined with data from the other sensors 30A, 30B, and/or 30C, or multiple other sensors as represented by 30N, in order to "fine tune" the predictive accuracy of the controller 50 when ascertaining the vulnerability of the passenger 11 to forces during actuation of the passenger restraint systems 18.

In accordance with the present disclosure, the controller 50 executes computer-readable instructions embodying the method 100 to perform the various functions described herein. The term "controller" and related terms such as microcontroller, electronic control unit, etc., refer to one or various combinations of Application Specific Integrated Circuit(s) (ASIC), Field-Programmable Gate Array (FPGA), electronic circuit(s), central processing unit(s), e.g., microprocessor(s) and associated transitory and non-transitory memory/storage component(s).

The controller 50 of FIGS. 1 and 2 is depicted schematically as having a processor 52 of one or more of such types, as well as memory 54 inclusive of non-transitory memory or tangible storage devices (read only, programmable read only, solid-state, random access, optical, magnetic, etc.). The memory 54, on which computer-readable instructions embodying the method 100 may be recorded, is capable of storing machine-readable instructions in the form of one or more software or firmware programs or routines, combinational logic circuit(s), input/output circuit(s) and devices, signal conditioning and buffer circuitry and other components that can be accessed by one or more processors to provide a described functionality.

Input/output circuit(s) and devices include analog/digital converters and related devices that monitor inputs from sensors, with such inputs monitored at a preset sampling frequency or in response to a triggering event. Software, firmware, programs, instructions, control routines, code, algorithms, and similar terms mean controller-executable instruction sets including calibrations and look-up tables. Each controller executes control routine(s) to provide desired functions. Ultimately, the controller 50 outputs a control signal (arrow $CC_O$) to one or more of the passenger restraint systems 18 described herein to regulate an actual capacity setting thereof. An exemplary approach will now be described with reference to FIG. 3.

Figure 3:
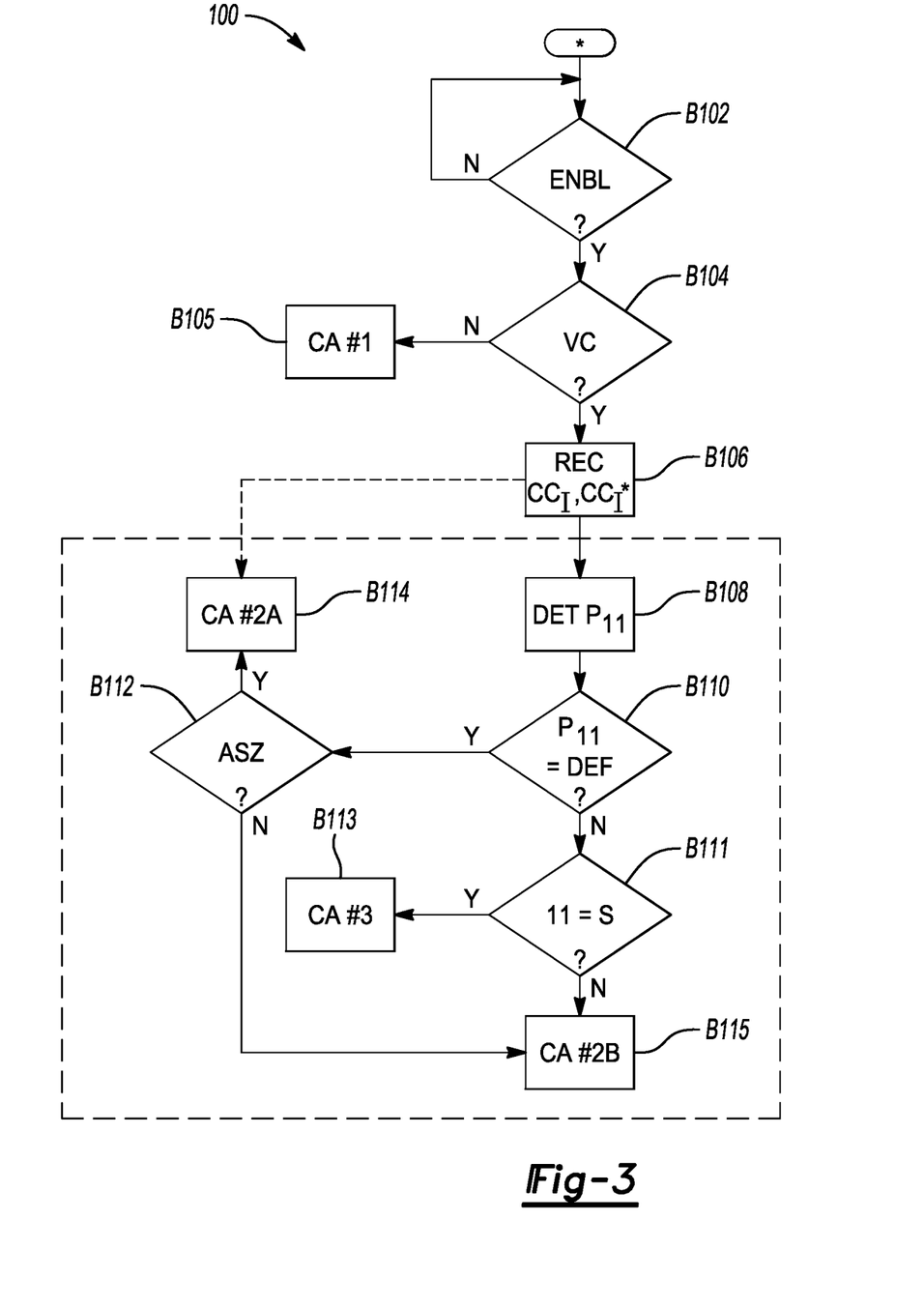
FIG. 3 is a flow chart illustrating an embodiment of a method for dynamically adjusting actual capacities of the various passenger restraint systems shown in FIGS. 1 and 2.

Referring now to FIG. 3, the method 100 in accordance with the present disclosure is executed by the processor 52 of FIG. 1 from non-transitory elements of the memory 54, e.g., from ROM, to situationally adjust actual capacity settings of one or more of the various passenger restraint systems 18 described above. Given a set of inputs indicative of each passenger's level of vulnerability or frailty, that is, the controller 50 may assign weights to the various factors to individually classify prospective or actual passengers into one of a plurality of biometric vulnerability classes. The capacity settings for the passenger restraint systems 18 of FIG. 2 are thereafter adjusted by the controller 50 based on the corresponding biometric vulnerability class.

As will be appreciated, the method 100 may be performed in a range of manners to provide a desired level of control across a possible continuum of actual capacity settings of the restraint systems 18. In general, the method 100 includes receiving, via the controller 50, biometric vulnerability classifier signal(s) indicative of vulnerability characteristics of a passenger seated in an interior of the motor vehicle. In response to the biometric vulnerability classifier signal(s) and a detected vehicle event requiring an actuation of the passenger restraint system(s) 18, the method 100 also includes automatically adjusting an actual capacity setting of the passenger restraint system(s) 18 via the controller 50.

An example of the method 100 commences after initialization (*) of the controller 50, e.g., a key-on event, with block B102. As used herein, "block" refers to corresponding logic, code, algorithms, or subroutines used to implement the corresponding functions. At block B102, the controller 50 of FIGS. 1 and 2 determines if vulnerability assessment and restraint control is to be fully enabled ("ENBL?"). For instance, the controller 50 may evaluate one or more assessment conditions. Exemplary assessment conditions may include a present dynamic state of the motor vehicle 10, which in turn may entail determining if the motor vehicle 10 is in a drive mode and is presently in motion, etc. Other possible assessment conditions may be used in different embodiments, including possibly using weight, visual, infrared (IR) or thermal signatures, position, machine vision, and/or other available sensory data indicative of the presence of one or more passengers 11, 11R in the vehicle interior 14 of FIG. 1, regardless of their present vulnerability status. The method 100 returns to block B102 when assessment and control are not enabled, and to block B104 in the alternative.

At block B104 ("VC" ?) the controller 50 next determines whether a detected passenger 11, 11R has a particular vulnerability warranting capacity adjustments in accordance with the present disclosure, e.g., musculoskeletal frailty or small occupant size as examples noted above. Block B104 could be implemented in various ways. As noted above, a user may optionally program baseline vulnerability levels for each prospective passenger 11 of the motor vehicle 10 shown in FIG. 1. Alternatively, the passengers 11 could be new/first time passengers lacking such a baseline. In either case, block B104 may entail using the sensor suite 30 of FIG. 2 to detect one or more "characteristic markers" associated to some degree with or predictive of vulnerability or frailty of each one of the passengers 11 as compared to stored data or remotely located data.

Exemplary characteristic markers include appearance traits such as the presence of the cast 23 of FIG. 1, or of a neck brace 230, slings, splints, or other medical devices on the passenger 11. Characteristic markers could also include, e.g., hair color, hairline recession, wrinkles or sagging skin, height, posture, weight, height-to-weight/girth ratio, gender by body shape, etc. Detecting the vulnerability characteristics may occur using the onboard sensor suite 30 of FIG. 2, e.g., using the remote sensor(s) 30B to detect a physical appearance of the passenger 11 as noted above, or detecting the cast 23 or a splint, brace, immobilizer, etc. located on a body part of the passenger 11. Such information could be optionally augmented by data from the optional biosensors 30C or any of the other sensors 30A, 30D-N of FIG. 2 as noted above.

As these and other characteristic markers may have a greater or lesser value when predicting vulnerability of a given passenger 11, the controller 50 may in some implementations assign a relative weight to each characteristic marker. For example, for a nominal set of characteristic markers $M_1$, $M_2$, and $M_3$, the controller 50 could optionally calculate a vulnerability score (S), e.g., $S = w_1 M_1 + w_2 M_2 + w_3 M_3$. The associated weights $w_1$, $w_2$, and $w_3$ could be determined offline and stored in memory 54 of the controller 50, e.g., in a data lookup table. The controller 50 in such an embodiment could then measure or otherwise collect the characteristic markers $M_1$, $M_2$, and $M_3$ within the vehicle interior 14 of FIG. 1 or offline/remotely via a remote source, for example the user device 25 and app 26, extract the associated weights $w_1$, $w_2$, and $w_3$, and calculate the above-summarized vulnerability score.

Additionally, the controller 50 in this and other possible embodiments could optionally set up multiple different biometric vulnerability categories, in which case the method 100 may include automatically classifying a plurality of potential passengers 11 into a corresponding one of the biometric vulnerability categories. For example, for each nominal characteristic marker $M_1$, $M_2$, and $M_3$ in this simplified example, the controller 50 could normalize the collected data into a unitless value ranging between 0 and 1. The associated weights $w_1$, $w_2$, and $w_3$ may thereafter be applied to such normalized values to calculate the vulnerability score for a given passenger 11. Each of the biometric vulnerability categories could have an assigned vulnerability score range, with each of the categories also having a corresponding capacity adjustment level to be applied to the passenger restraint system(s) 18 as set forth below. The method 100 proceeds to block B106 if a potentially vulnerable passenger 11 is detected. The method 100 proceeds in the alternative to block B105 when the passenger 11, 11A is deemed to be a low-vulnerability class.

Block B105 ("CA #1") includes executing a first control action in response to the determination at block B104 that the passenger 11 is not vulnerable. As contemplated herein, block B105 may include actuating or deploying one or more of the passenger restraint systems 18 in an unfettered manner, i.e., in a manner that would ordinarily occur absent the control refinements of the present teachings. Actions taken in block B105 could include, e.g., actuating or deploying one or more of the passenger restraint systems 18 described herein, using a maximum default setting for the impact severity being experienced, such as for the seatbelt pretensioner 180 and/or the energy-absorbing device 280 connected to the seatbelt 18A (see FIG. 2), an airbag, an actuatable or deployable seat device, etc.

Although omitted for illustrative simplicity, Block B105 in one or more embodiments may also contain a version of the logic of blocks B108-B115 described below without the vulnerability adjustments being made. That is, all of the described actions would ordinarily be performed for a non-vulnerable occupant.

Block B106 of FIG. 3 ("REC $CC_1$, $CC_1$*") includes receiving the biometric vulnerability classifier signal(s) indicative of the vulnerability characteristics of the passenger 11 seated within the vehicle interior 14 shown in FIG. 1. Block B106 may include transmitting the biometric vulnerability classifier signal(s) (arrows $CC_1$, $CC_1$*) to the controller 50, e.g., from the onboard sensor suite 30, or self-generating the biometric vulnerability classifier signal(s) (arrows $CC_1$, $CC_1$*) in response to the evaluation performed in block B104.

The method 100 in the illustrated embodiment of method 100 proceeds to block B108, with other possible/simplified embodiments proceeding in the alternative to block B114.

At block B108 ("DET $P_{11}$"), the controller 50 may optionally determine a position of the passenger 11 in free space within the vehicle interior 14. For example, one or more sensors of the sensor suite 30 shown in FIG. 2 could be used to detect the passenger 11 and ascertain a corresponding position. The position may correspond to a center-of-mass, the position may be a surface of the occupant closest to the sensor suite 30, or the position may be a point cloud providing an estimate of the total space occupied by the passenger 11.

When the passenger restraint system 18 includes one or more of the seatbelts 18A of FIG. 1, the method 100 at block B108 may optionally include detecting the buckled state of the seatbelt 18A, e.g., from a seatbelt buckle sensor (not shown) positioned therein or thereon as appreciated in the art. The controller 50 then automatically adjusts the actual capacity setting of the seatbelt 18A based at least partially on its buckle state. A positive buckle state could enable seatbelt mounted restraints to be actuated or deployed in a crash above a certain severity. A positive buckle state could trigger detection of a position of a shoulder belt relative to the torso of the passenger, e.g., using the position sensor or an embedded sensor in the seatbelt webbing. Actions could be taken when the shoulder belt is not properly positioned, or if the passenger is in a precarious position, such as not sitting in a vertical position relative to the vehicle seat. The method 100 proceeds to block B110 when the position of the passenger 11, 11A has been determined, and once the seatbelt buckle status and the shoulder belt position has been determined if that step is included.

Block B110 ("$P_{11}$=DEF?") includes determining if the position of the passenger 11 is definite, i.e., the passenger 11 is not obscured. Block B110 could include comparing a resolution of camera images or other positional data to clarity thresholds, for instance, to determine if the position of the passenger 11 is within an allowable tolerance or a certain surface area of the passenger can be directly viewed by the sensor. The method 100 proceeds to block B112 when the position is definite/the passenger 11 is not clearly observed, and to block B111 in the alternative.

Block B111 ("11=S?") may include optionally determining whether the detected passenger 11 is below a calibrated size threshold, i.e., is objectively "small". Such a determination is possibly indicative of the presence of a child or other person of small stature. Detecting the vulnerability characteristics of the passenger 11 in accordance with block B111 may include detecting a Child Restraint System (CRS), e.g., a forward-facing CRS, a rearward facing CRS, or a child bed CRS. This could occur based on signals or responses from an RF tag or a key switch disable state, for instance. The method 100 proceeds to block B113 when the detected passenger 11 is below the size threshold, and to block B115 in the alternative.

At block B112 ("ASZ?"), the controller 50 may determine whether the passenger 11 is located at least partially within a defined airbag suppression zone (ASZ). For instance, the controller 50 may be programmed with 3D boundaries within the vehicle interior 14 of FIG. 1 in close proximity to a stowed airbag system 18B. The method 100 proceeds to block B114 when a head, torso, neck, or other vulnerable part of the passenger 11 is partially within such a defined ASZ. When the passenger 11, such as for example the passenger's head, neck, and body regions, is detected as being outside of the ASZ, however, the method 100 proceeds instead to block B115.

Block B113 ("CA #3") includes executing a control action in response to detection of a small/undersized passenger 11 with an indefinite 3D position within the vehicle interior 14. When a forward-facing CRS is present at block B111, for instance, the controller 50 could suppress one or more of the restraint systems 18 or change an output for an airbag or enable a low level output for a seatbelt actuatable or deployable device, e.g., by adjusting the setting of the seatbelt pretensioner 180 and/or the energy-absorbing device 280 connected to the seatbelt 18A shown in FIG. 2 to less than a maximum possible setting. Actions to change an airbag output may include adjusting one or more of an inflator output, an inflated cushion depth, a deployment time, and/or a vent size of the deployable airbag system 18B. Thus, the control action in block B113 could entail suppressing the capacity level of one or more of the passenger restraint systems 18 to a calibrated level or a no actuation or deployment level suitable for such passengers 11. Adjusting the actual capacity setting in block B113 could occur via the controller 50 based on the corresponding biometric vulnerability class noted above, e.g., with more aggressive control and higher inflation/activation levels being used for less vulnerable passengers 11 and less aggressive control and lower inflation/activation levels being used for more vulnerable passengers 11.

For instance, in a two-stage embodiment of the inflatable airbag system 18B, block B113 may entail triggering just one inflation stage to provide a lower total inflation force, e.g., about 70% of a total possible inflation force. Block B113 could include opening the vents 480 of FIG. 2 to a predetermined vent size to ensure faster/greater venting and thus a softer impact with the deployed airbag system 18B. In addition, Block B113 could include either not releasing or releasing the extendable tethers 580 of FIG. 2 adjusting the occupant's contact with the deployed airbag system 18B. Other responses could be enacted for different restraint systems 18, including possibly adjusting a setting of the pretensioner 180 and/or energy-absorbing device 280 shown in FIG. 2, and/or adjusting an energy absorption or actuatable/deployable device in the seat, either alone or in conjunction with size-based suppression of the inflatable airbag system(s) 18B.

At block B114 ("CA #2A"), the controller 50 may execute a control action similar to that of block B113, however in this case performing adjustments in accordance with the relevant state of the passenger 11. That is, block B114 is executed when the passenger 11 is not obscured and some vulnerable part of the passenger 11 is situated in the ASZ, as determined in blocks B110 and B112, respectively. Alternatively, the method 100 may be performed in some embodiments without determining the position of the passenger 11 within the vehicle interior 14.

Under such conditions, the controller 50 may adjust one or more of the inflator output, the inflated cushion depth, deployment time, and/or the vent size based on whether at least a portion of the passenger 11 is present within the ASZ. This could entail suppressing inflation of one or more of the inflatable airbag system(s) 18B based on either the occupant's detected position relative to the ASZ boundary or the biometric vulnerability classifier signal(s) and a detected vehicle event requiring deployment of the passenger restraint system(s) 18. As with blocks B113 and B115, the performance of block B114 may entail automatically adjusting an actual capacity setting of the passenger restraint system(s) 18 via the controller 50 to a lesser degree than the levels made in block B105.

Capacity adjustments in block B114 could include suppressing activation of certain passenger restraint systems 18 in close proximity to the passenger 11 whose vulnerable body regions are partially within the ASZ of block B112, for instance. When block B114 is arrived at from block B106 directly, the control actions taken at block B114 could possibly include selecting the appropriate capacities from a lookup table indexed by the passenger 11 and his or her corresponding biometric vulnerability class as noted above.

The controller 50 could thereafter adjust the actual capacity setting(s) based on the corresponding biometric vulnerability class.

Block B115 ("CA #2B") is analogous to block B114, and may be performed when a passenger 11 of small size/stature is not present, i.e., from block B111, or when a passenger having a definite ascertained position is confirmed not to be within the ASZ (block B112). In such an event, the control action performed in block B115 could include adjusting the actual capacity setting(s) of the passenger restraint systems 18 to a lesser degree than the control actions performed in block B105.

Relative to block B111, where the passenger 11 is deemed by the controller 50 not to be small, block B115 has the additional information regarding obscure position and size of the passenger 11. As a result, actions taken in block B115 may differ from those of blocks B105 in some embodiments, or blocks B105 and B115 may be identical. As the capacity adjustments contemplated herein as considered to be "tunable" as part of a response continuum in addition to being stepped or binary ON/OFF decisions, one skilled in the art will appreciate that the control actions of blocks B105 and B113-B115 may be calibratable for a given construction of the motor vehicle 10 and its various passenger restraint systems 18.

Likewise, for each block B105, B113, B114, and B115 the controller 50 may adjust the actual capacity setting based on the corresponding biometric vulnerability class as described above. That is, passenger restraint systems 18 in proximity to a passenger 11 having a first set of classified vulnerabilities could possibly impart higher or lower activation forces relative to another passenger restraint system 18 located in proximity to a differently located passenger having a second set of vulnerabilities. A programmed operating point would be selected during operation of the motor vehicle 10 along a permissible continuum or operating range of possible settings, in other words, to fine-tune performance of the various passenger restraint systems 18 to account for actual limitations or vulnerabilities of the passengers 11 for whom these restraint systems 18 are intended to restrain.

As will be appreciated by those skilled in the art, the above teachings enable passenger-specific levels of control during actuation or deployment of a passenger restraint system 18 aboard a motor vehicle 10. Unlike prior art systems that selectively disable certain devices such as front airbags based on static weight thresholds, the present approach provides a level of refinement by classifying the unique biometric vulnerability of passengers 11 of the motor vehicle 10 and controlling capacities of the restraint systems 18 along a permissible continuum in accordance with the classification.

Other refinements may be included within the scope of the disclosure, including but not limited to classification and consideration of non-human occupants such as pets or objects, with the controller 50 possibly being calibratable for each of these possible passenger types. The solutions described herein ultimately allow the protection afforded by the various passenger restraint systems 18 to a specific passenger 11 to be precisely matched to their unique vulnerabilities in the event of a restraint actuation or deployment. These and other attendant benefits will be readily appreciated by those skilled in the art in view of the foregoing disclosure.

Within this application, the term "at least one" means any single item, more than one item but fewer than all referenced items, or all referenced items can be used depending on the embodiment, and does not necessarily mean that all of the referenced items have to be used.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

What is claimed is:

1. A method for controlling a passenger restraint system aboard a motor vehicle having a vehicle interior, the method comprising:
   receiving, via a controller, one or more biometric vulnerability classifier signals indicative of vulnerability characteristics of a passenger seated in the vehicle interior; and
   in response to the one or more biometric vulnerability classifier signals and a detected vehicle event requiring an actuation of the passenger restraint system, automatically adjusting an actual capacity setting of at least a portion of the passenger restraint system via the controller.

2. The method of claim 1, the method further comprising:
   detecting the vulnerability characteristics using an onboard sensor suite of the motor vehicle, the onboard sensor suite including an in-seat sensor connected to a vehicle seat within the vehicle interior, a remote sensor connected to a structure within the vehicle interior, and/or a biometric sensor located in the vehicle interior.

3. The method of claim 2, wherein detecting the vulnerability characteristics includes detecting a physical appearance of the passenger using the onboard sensor suite.

4. The method of claim 2, wherein detecting the vulnerability characteristics occurs based on one or more of body disabilities, gender, and age of the passenger, and includes detecting one or more of: a cast, a splint, or a brace located on a body part of the passenger, a size, a hair color, wrinkles, hair recession, sagging skin, and/or a posture of the passenger.

5. The method of claim 2, wherein detecting the vulnerability characteristics includes detecting a Child Restraint System (CRS).

6. The method of claim 2, wherein the onboard sensor suite includes the biometric sensor, and wherein detecting the vulnerability characteristics includes detecting an internal characteristic of the passenger using the biometric sensor.

7. The method of claim 1, wherein the passenger restraint system includes a seatbelt, the method further comprising:
   detecting a buckled state of the seatbelt; and
   automatically adjusting the actual capacity setting based at least partially on the buckled state.

8. The method of claim 7, wherein the seatbelt contains a shoulder belt webbing portion whose position can be sensed by a remote sensor, the method further comprising:
   detecting the shoulder belt webbing location via the remote sensor; and
   automatically adjusting the actual capacity setting based at least partially on the shoulder belt location relative to the passenger.

9. The method of claim 7, wherein adjusting the actual capacity setting includes adjusting a setting of at least one of a seatbelt pretensioner and a seatbelt energy-absorbing device connected to the seatbelt.

10. The method of claim 1, wherein the passenger restraint system includes an airbag system, and wherein adjusting the actual capacity setting includes adjusting an inflator output, an inflated cushion depth, a deployment time, and/or a vent size of the airbag system.

11. The method of claim 10, wherein the controller is operable for enforcing an airbag suppression zone (ASZ) in a defined proximity to the airbag system, and wherein adjusting the actual capacity setting includes adjusting the inflator output, the inflated cushion depth, the deployment time, and/or the vent size based on whether at least a portion of the passenger is present within the ASZ.

12. The method of claim 1, wherein the passenger restraint system includes an actuatable seat system, and wherein adjusting the actual capacity setting includes modifying actuation characteristics of a seating surface position and/or a head restraint location of the adjustable seat system.

13. A motor vehicle comprising:
a vehicle body defining a vehicle interior;
a vehicle seat positioned in the vehicle interior; and
a sensor suite having at least one of an in-seat sensor connected to the vehicle seat, a remote sensor connected to a structure within the vehicle interior, and a biometric sensor located in the vehicle interior;
a passenger restraint system positioned in the vehicle interior; and
a controller operable for controlling an actual capacity setting of the passenger restraint system, wherein execution of instructions by a processor of the controller causes the processor to:
detect vulnerability characteristics of a passenger of the motor vehicle using the sensor suite;
generate one or more biometric vulnerability classifier signals indicative of the vulnerability characteristics; and
in response to the one or more biometric vulnerability classifier signals and a detected vehicle event requiring an actuation of the passenger restraint system, automatically adjust an actual capacity setting of at least a portion of the passenger restraint system.

14. The motor vehicle of claim 13, wherein the sensor suite includes a remote sensor, and wherein the execution of the instructions causes the processor to detect the vulnerability characteristics at least in part by detecting a physical appearance characteristic of the passenger using the remote sensor.

15. The motor vehicle of claim 13, wherein the execution of the instructions causes the processor to detect a Child Restraint System (CRS) as at least one of the vulnerability characteristics.

16. The motor vehicle of claim 13, wherein the passenger restraint system includes a seatbelt, and wherein the execution of the instructions causes the processor to:
detect a buckled state of the seatbelt; and
adjust the actual capacity setting based on the buckled state, the actual capacity setting including at least one of a setting of a seatbelt pretensioner and a seatbelt energy-absorbing device.

17. The motor vehicle of claim 13, wherein the passenger restraint system includes an airbag system, and wherein the execution of the instructions causes the processor to:
adjust the actual capacity setting by adjusting an inflator output, an inflated cushion depth, a deployment time, and/or a vent size of the airbag system.

18. The motor vehicle of claim 13, wherein the passenger restraint system includes an adjustable seat system, and wherein adjusting the actual capacity setting includes modifying actuation characteristics of a seating surface position and a head restraint location of the adjustable seat system.

19. A method for controlling a passenger restraint system aboard a motor vehicle, comprising:
detecting vulnerability characteristics of one or more passengers of the motor vehicle using a sensor suite, the sensor suite including an in-seat sensor connected to a passenger seat of the motor vehicle, a remote sensor, and/or a biometric sensor positioned within an interior of the motor vehicle, wherein detecting the vulnerability characteristics includes detecting a physical characteristic and/or an internal characteristic of each of the one or more passengers using the in-seat sensor and/or the remote sensor, respectively;
generating one or more biometric vulnerability classifier signals indicative of vulnerability characteristics indicative of the passenger;
receiving the one or more biometric vulnerability classifier signals via a controller of the motor vehicle; and
in response to the one or more biometric vulnerability classifier signals and a detected vehicle event requiring a deployment of the passenger restraint system, automatically adjusting an actual capacity setting of the passenger restraint system via the controller, wherein the passenger restraint system includes a seatbelt and a deployable airbag system.

20. The method of claim 19, wherein adjusting the capacity setting of the passenger restraint system includes reducing an output of a component of the passenger restraint system, reducing a size of the passenger restraint, reducing an applied force level of the passenger restraint system, and/or suppressing activation of the passenger restraint system.

* * * * *